(12) United States Patent
Li (10) Patent No.: US 10,147,010 B2
(45) Date of Patent: Dec. 4, 2018

(54) SMART SHOE (71) Applicant: BOE Technology Group Co., Ltd., Beijing (CN)

(72) Inventor: Wenbo Li, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 15/324,349

(22) PCT Filed: Jan. 6, 2016

(86) PCT No.: PCT/CN2016/070250
§ 371 (c)(1),
(2) Date: Jan. 6, 2017

(87) PCT Pub. No.: WO2017/024757
PCT Pub. Date: Feb. 16, 2017

(65) Prior Publication Data
US 2017/0213095 A1    Jul. 27, 2017

(30) Foreign Application Priority Data
Aug. 10, 2015 (CN) .......................... 2015 1 0487756

(51) Int. Cl.
*A61B 5/117* (2016.01)
*G06K 9/00* (2006.01)
(Continued)

(52) U.S. Cl.
CPC ........ *G06K 9/00885* (2013.01); *A43B 3/0005* (2013.01); *A43B 3/0015* (2013.01);
(Continued)

(58) Field of Classification Search
CPC ..... A61B 5/117; A61B 5/1171; A61B 5/1174; A61B 5/68; A61B 5/6801; A61B 5/6802;
(Continued)

(56) References Cited

U.S. PATENT DOCUMENTS 9,433,357 B2 * 9/2016 Yuen .................. G06F 19/3418
2004/0042642 A1 3/2004 Bolle et al.
(Continued)

FOREIGN PATENT DOCUMENTS

CN 201491798 U 6/2010
CN 202504369 U 10/2012
(Continued)

OTHER PUBLICATIONS

International Search Report and Written Opinion of International Application No. PCT/CN2016/070250, dated May 10, 2016, 13 pages.
(Continued)

*Primary Examiner* — Andrew Bee
(74) *Attorney, Agent, or Firm* — Westman, Champlin & Koehler, P.A.

(57) ABSTRACT

Embodiments of the present disclosure relate to the field of shoe production. There provides a smart shoe which has an identification function. The smart shoe includes an upper, a shoe sole and a foot sole print recognition sensor disposed in the shoe sole; the foot sole print recognition sensor is configured to acquire foot sole print information of a user who wears the smart shoe.

18 Claims, 9 Drawing Sheets

(51) Int. Cl.
*A61B 5/00* (2006.01)
*A61B 5/1171* (2016.01)
*A61B 5/1174* (2016.01)
*A43B 3/00* (2006.01)
*A43B 3/24* (2006.01)
*A43B 21/24* (2006.01)
*A43B 21/437* (2006.01)

(52) U.S. Cl.
CPC ............ *A43B 3/0021* (2013.01); *A43B 3/24* (2013.01); *A43B 21/24* (2013.01); *A43B 21/437* (2013.01); *A61B 5/117* (2013.01); *A61B 5/1171* (2016.02); *A61B 5/1174* (2013.01); *A61B 5/68* (2013.01); *A61B 5/6801* (2013.01); *A61B 5/6802* (2013.01); *A61B 5/6804* (2013.01); *A61B 5/6807* (2013.01); *G06K 9/00* (2013.01); *G06K 9/00362* (2013.01)

(58) Field of Classification Search
CPC ...... A61B 5/6804; A61B 5/6807; G06K 9/00; G06K 9/00362; G06K 9/00885
See application file for complete search history.

(56) References Cited

U.S. PATENT DOCUMENTS

| | | | | |
|---|---|---|---|---|
| 2005/0049816 A1* | 3/2005 | Oda | ............... | A43D 1/025 702/127 |
| 2008/0203144 A1 | 8/2008 | Kim | | |
| 2010/0324455 A1* | 12/2010 | Rangel | ............... | A43B 7/147 600/592 |
| 2012/0086550 A1* | 4/2012 | LeBlanc | ............... | A61B 5/1038 340/5.82 |
| 2015/0157087 A1 | 6/2015 | Blumenthal et al. | | |
| 2015/0177053 A1* | 6/2015 | Bagan | ............... | A61B 5/0002 177/2 |
| 2017/0109593 A1* | 4/2017 | Schueren | ............... | G06K 9/00892 |
| 2017/0199606 A1* | 7/2017 | Liu | ............... | G06F 3/0412 |

FOREIGN PATENT DOCUMENTS

| | | | | |
|---|---|---|---|---|
| CN | 202774398 U | | 3/2013 | |
| CN | 203137209 U | | 8/2013 | |
| CN | 203194665 U | | 9/2013 | |
| CN | 103799618 A | | 5/2014 | |
| CN | 204105019 U | | 1/2015 | |
| CN | 104346548 A | | 2/2015 | |
| CN | 104408624 A | | 3/2015 | |
| CN | 105029823 A | | 11/2015 | |
| CN | 204908154 U | * | 12/2015 | ............ A34B 13/14 |
| CN | 204908154 U | | 12/2015 | |
| KR | 100702613 B1 | | 3/2007 | |

OTHER PUBLICATIONS

English translation of Box No. V of the Written Opinion for the International Searching Authority for International Application No. PCT/CN2016/070250, 2 pages.

First Office Action, including Search Report, for Chinese Patent Application No. 201510487756.8, dated Jul. 18, 2016, 13 pages.

* cited by examiner

SMART SHOE

CROSS-REFERENCE TO RELATED APPLICATION

This application is a Section 371 National Stage Application of International Application No. PCT/CN2016/070250, filed on Jan. 6, 2016, entitled "Smart Shoe", which has not yet published, which claims priority to Chinese Application No. 201510487756.8, filed on Aug. 10, 2015, incorporated herein by reference in their entirety.

BACKGROUND

1. Technical Field

Embodiments of the present disclosure relate to the field of shoe production, and particularly to a smart shoe.

2. Description of the Related Art

With improvement of living standards, people's consumption level is accordingly increasing, and especially, female beauties will buy some luxury goods such as shoes, bags and so on.

In some places such as gym, swimming pool, beauty salons and the like, compared to bags which are portable or can be stored in the safe cabinet, shoes will be uniformly stored into some open areas, so that, on one hand, there is a possible risk of wearing the wrong shoe, on the other hand, the shoe with higher value will be thieved, in this case, it is difficult for the shoe owner to find his/her shoes, which will bring greater losses.

SUMMARY

According to embodiments of the present disclosure, there is provided a smart shoe comprising an upper, a shoe sole and a foot sole print recognition sensor disposed in the shoe sole; wherein, the foot sole print recognition sensor is configured to acquire foot sole print information of a user who wears the smart shoe.

In some embodiments, the foot sole print recognition sensor comprises any one of a radio frequency type foot sole print recognition sensor, an optical-type foot sole print recognition sensor, a capacitive-type foot sole print recognition sensor and an ultrasonic-type foot sole print recognition sensor.

In some embodiments, the smart shoe further comprises a processor, a storage and a first alarm; the processor is connected respectively to the foot sole print recognition sensor, the storage and the first alarm; the storage is configured to store foot sole print information; the processor is configured to receive the foot sole print information acquired by the foot sole print recognition sensor, to match the received foot sole print information with the stored foot sole print information in the storage, and, to send an alarm signal if they do not match with each other; and the first alarm is configured to receive the alarm signal sent by the processor and to alarm.

In some embodiments, the smart shoe further comprises a first communication module; the first communication module is configured to transmit the foot sole print information acquired by the foot sole print recognition sensor to an external terminal device; or the first communication module is also configured to transmit the alarm signal sent by the processor to the external terminal device when the smart shoe further comprises the first alarm.

In some embodiments, the smart shoe further comprises a heel comprising a base part of heel and at least one connecting parts of heel, and, the connecting parts of heel and the base part of heel are arranged to be nested into one another from top to bottom in sequence while the base part of heel is fixedly connected to a rear end of the shoe sole; wherein, the base part of heel is hollow, and all the connecting parts of heel, at most excepting the one which is farthest away from the base part of heel, are hollow.

In some embodiments, the smart shoe further comprises an elastic support disposed at a side face of the connecting part of heel, being retractable into the connecting part of heel or being stretchable from the connecting part of heel, and being configured to secure the connecting part of heel stretched from the base part of heel or from another connecting part of heel, being disposed above the stretched connecting part of heel.

In some embodiments, the elastic support is in a wedge shape, and a cross sectional area of the elastic support is gradually decreased from top to bottom.

In some embodiments, a cross sectional area of a bottom of any one of the connecting parts of heel is greater than a cross sectional area of a top thereof.

In some embodiments, the connecting part of heel comprises a cylindrical main body and a cylindrical base, and a cross sectional area of the base is greater than that of the main body; and, central axes of the main body and of the base lie in one straight line.

In some embodiments, the smart shoe further comprises a pedometer configured to record walking data.

In some embodiments, the pedometer comprises a step-counting sensing module configured to acquire the walking data, a display module, and a control module configured to display, through the display module in real time, the walking data acquired by the step-counting sensing module.

In some embodiments, the walking data comprises number of steps and a travel time; the pedometer further comprises a switching button connected to the control module and configured to control, by the control module, the display module to display the number of steps or the travel time.

In some embodiments, in a case that the smart shoe comprises a heel, the control module is further configured to send a reminder instruction to the display module according to a height of the heel when the number of steps or the travel time is greater than a present value; and the display module is also configured to display the reminder instruction sent by the control module.

In some embodiments, the smart shoe further comprises a second alarm connected to the control module and configured to alarm according to the reminder instruction sent by the control module.

In some embodiments, the smart shoe further comprises a position sensor connected to the control module, being disposed at a location where the base part of heel contacts the shoe sole and outside of the base part of heel, and being configured to measure the height of the heel.

In some embodiments, the smart shoe comprises a second communication module connected to the pedometer and configured to transmit the walking data to an external terminal device.

In some embodiments, in a case that the smart shoe comprises a first communication module, the first communication module and the second communication module are the same one.

In some embodiments, the smart shoe further comprises a power supply module configured to provide an electric power, and a charging interface disposed on the base part of heel and configured for charging of the power supply module.

BRIEF DESCRIPTION OF THE DRAWINGS

In order to provide a more clear explanations of technical solutions in embodiments of the present disclosure or those in the prior art, there is provided a brief introduction of the attached drawings used in the following description of the embodiments or of the prior art. Obviously, the drawings mentioned in the following description belong to some embodiments of the present disclosure. However, for those skilled in the art, other drawings may be achieved on the basis of these attached drawings without involving any inventive steps.

DETAILED DESCRIPTION OF THE EMBODIMENTS

In order to provide a more clear understanding of technique solutions of embodiments of the present disclosure, the embodiments of the present disclosure will be further described hereinafter in detail and completely with reference to the attached drawings. Obviously, the embodiments illustrated in these drawings are only some of embodiments of the present disclosure, instead of all of the embodiments of the present disclosure. For those skilled in the art, other embodiments achieved by referring to the following embodiments without involving any inventive steps fall into the scope of the present disclosure.

Figure 1:
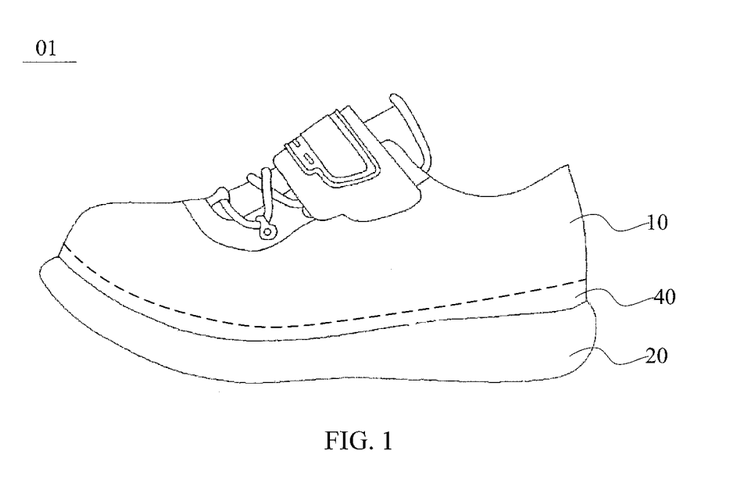
FIG. 1 is a schematic view of a first structure of a smart shoe according to an embodiment of the present disclosure.
Figure 2:
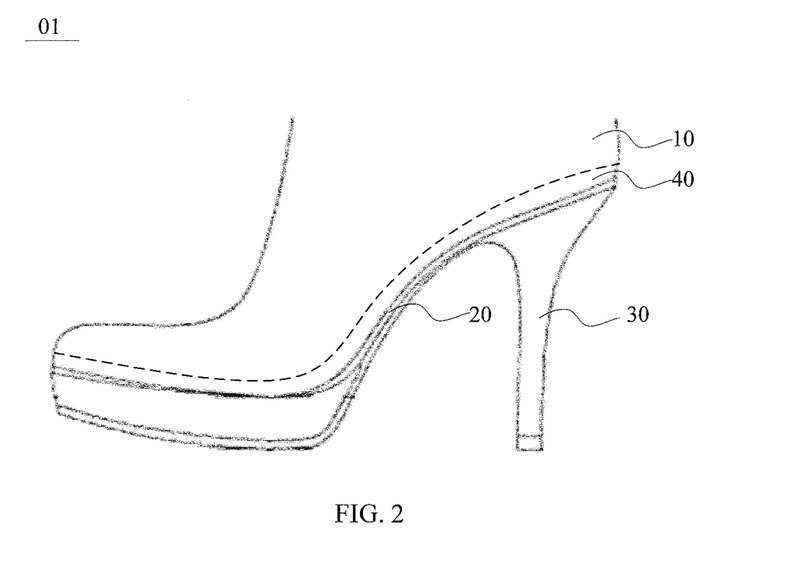
FIG. 2 is a schematic view of a second structure of a smart shoe according to an embodiment of the present disclosure.

Embodiments of the present disclosure provide a smart shoe 01. Referring to FIG. 1 and FIG. 2, the smart shoe 01 mainly comprises an upper 10, a shoe sole 20 and a foot sole print recognition sensor 40 disposed in the shoe sole 20; wherein, the foot sole print recognition sensor 40 is configured to acquire foot sole print information of a user who wears the smart shoe.

The foot sole print recognition sensor 40 may be an optical-type foot sole print recognition sensor, a capacitive-type foot sole print recognition sensor, an ultrasonic-type foot sole print recognition sensor, or a radio frequency type foot sole print recognition sensor, and so on.

The optical-type foot sole print recognition sensor mainly utilizes principle of light refraction and reflection. Once incident light is emitted onto valley lines of the foot sole print, a total reflection occurs while less light intensity of the reflected light will loss. Once the incident light is emitted onto ridge lines of the foot sole print, no total reflection occurs while more light intensity of the reflected light will loss. A gray level image of the foot sole print can be converted from identification of the reflected light.

The capacitive-type foot sole print recognition sensor mainly utilizes that different actual distances between valley lines and ridge lines of the foot sole print and the sensor will result in different capacitance values. A gray level image of the foot sole print can be converted by summarizing the different capacitance values.

The ultrasonic-type foot sole print recognition sensor firstly scans a surface of the foot sole print with a ultrasonic wave, measures a range of reflected signals in accordance with the acquired reflected signal, obtain depths of ridges of the foot sole print, and thus obtain a gray level image of the foot sole print.

The radio frequency type foot sole print recognition sensor mainly utilizes the foot sole itself serving as a control panel and as medium, to generate an extremely low radio frequency signal, of which the diffusion relates to valley lines and ridge lines of the foot sole print. The radio frequency type foot sole print recognition sensor detects this signal, so as to obtain a gray level image of the foot sole print.

It should be mentioned that, the foot sole print recognition sensor 40 may be disposed at a front end, namely where the foot sole of foot is to be located, of the shoe sole 20, or be disposed at a rear end, namely where the heel is to be located, of the shoe sole 20, or be disposed on the whole shoe sole 20. There is no limitation on this herein.

With the smart shoe provided by the embodiments of the present disclosure, the foot sole print information of a user who wears this shoe can be acquired by the foot sole print recognition sensor 40 disposed on the shoe sole 20. Every person's skin textures, including patterns, breakpoints and cross points, are different from one another, that is to say, each person owns his/her unique skin texture, accordingly, whether or not a person who is wearing a shoe is eligible to wear this shoe can be determined by means of identification of the foot sole print information, namely, the shoe is allowed to own an identification function to prevent losses caused by the loss of the shoe.

In consideration of existence of insulated materials such as shoe pad, sock and the like when the foot sole print recognition sensor 40 acquires foot sole print information, a radio frequency type foot sole print recognition sensor is preferred to be used in embodiments of the present disclosure.

Figure 3A:
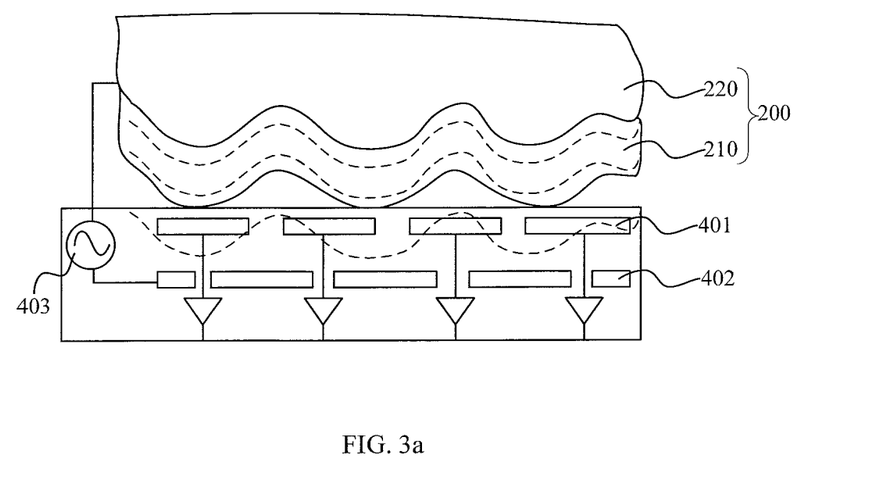
FIG. 3a is a schematic view showing working principle of a radio frequency type foot sole print recognition sensor in a smart shoe according to an embodiment of the present disclosure.

For a radio frequency type foot sole print recognition sensor, referring to FIG. 3a, it includes a plurality of radio frequency receiving electrodes 401 arranged in an array, and radio frequency signal reference electrodes 402 disposed below the radio frequency receiving electrodes 401 and serving as an excitation signal reference plane, and also includes a radio frequency signal generation unit 403 configured to generate a radio frequency signal.

Figure 3B:
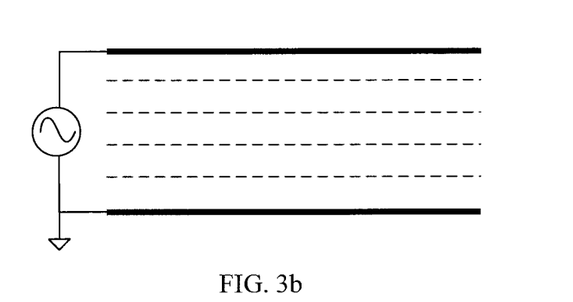
FIG. 3b is a schematic view showing the radio frequency type foot sole print recognition sensor shown in FIG. 3a, when no foot sole print recognition is implemented.
Figure 3C:
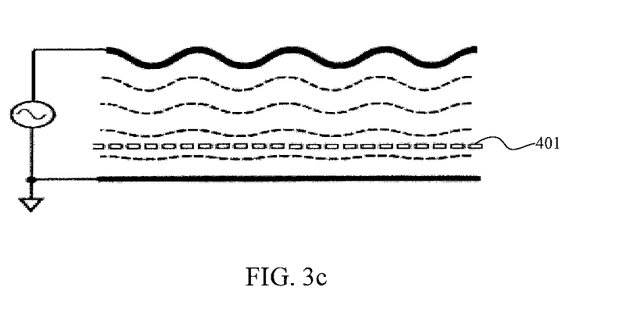
FIG. 3c is a schematic view showing the radio frequency type foot sole print recognition sensor shown in FIG. 3a, when a foot sole print recognition is implemented.

When no foot sole print is presented above the radio frequency type foot sole print recognition sensor, referring to FIG. 3b, a parallel electric potential is created. In combination with FIG. 3a and FIG. 3c, when a foot sole 200 is presented above the radio frequency type foot sole print recognition sensor, the radio frequency type foot sole print recognition sensor generates a radio frequency signal, the radio frequency signal is transferred to a foot sole skin inner layer (namely a conductive dermis layer 220) located in a greater depth through non-conductive dead skin cells in the cuticular layer 210 of the foot sole 200. The radio frequency signal becomes bending under interference of the dermis layer 220. Since structures between the foot sole dermis layer 220 and the cuticular layer 210 correspond to those of valley lines and ridge lines in the foot sole cuticular layer, when a reflecting signal that is reflected by the structure between the foot sole dermis layer 220 and the cuticular layer 210 to the radio frequency receiving electrode 401 is detected, a gray level image of the foot sole print can be achieved.

Figure 4:
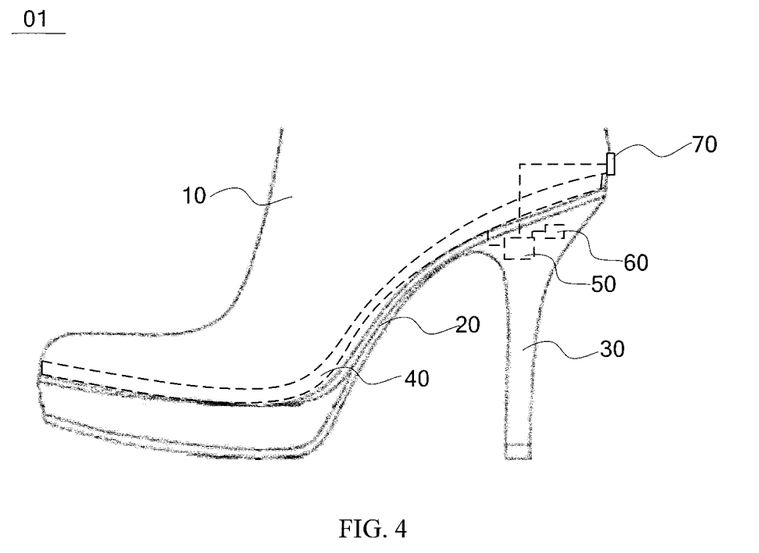
FIG. 4 is a schematic view of a third structure of a smart shoe according to an embodiment of the present disclosure.

Preferably, referring to FIG. 4, the smart shoe 01 further comprises a processor 50, a storage 60 and a first alarm 70; and, the processor 50 is connected respectively to the foot sole print recognition sensor 40, the storage 60 and the first alarm 70.

The storage 60 is configured to store the foot sole print information. Here, the foot sole print information stored in the storage 60 is used for authenticating foot sole print information of the user.

The processor 50 is configured to receive the foot sole print information acquired by the foot sole print recognition sensor 40, to match the foot sole print information with the stored foot sole print information in the storage 60, and, to send an alarm signal if not match.

The first alarm 70 is configured to receive the alarm signal sent by the processor 50 and to alarm.

Here, the first alarm 70 may be a buzzer.

It should be mentioned that, locations of the processor 50, the storage 60 and the first alarm 70 are not limited in these embodiments of the present disclosure, and these can be set according to types of the shoes, as long as use of the shoe is not affected and the aesthetic appearance of the shoe is guaranteed to the greatest degree.

In embodiments of the present disclosure, the processor 50 is configured to compare and match foot sole print information of a person who wears the smart shoe with the foot sole print information pre-stored in the storage 60. If match, it is said that the current user is the authenticated user and the processor 50 will not perform any operation. If not match, it is said that the current user is a non-authenticated user and thus the first alarm 70 will alarm, to give a real time reminder to the owner of the shoe, for preventing loss of the shoe.

In an example, the acquired foot sole print information is recorded, in the form of a gray level image of the foot sole print, by the foot sole print recognition sensor 40.

Herein, the abovementioned matching process may be performed as follows: the processor 50 receives the gray level image of the foot sole print, sent by the foot sole print recognition sensor 40, implements, based on the gray level image of foot sole print, a pre-processing, a binaryzation, a refinement and the like, then, extracts characteristic points, and then compares and matches the extracted characteristic points with the foot sole print stored in the storage 60.

Upon the above, preferably, the smart shoe may further comprise a first communication module 80 configured to transmit the foot sole print information acquired by the foot sole print recognition sensor 40 to an external terminal device.

Or, the first communication module 80 is configured to transmit the alarm signal sent by the processor 50 to the external terminal device when the smart shoe further comprises the first alarm 70.

Figure 5A:
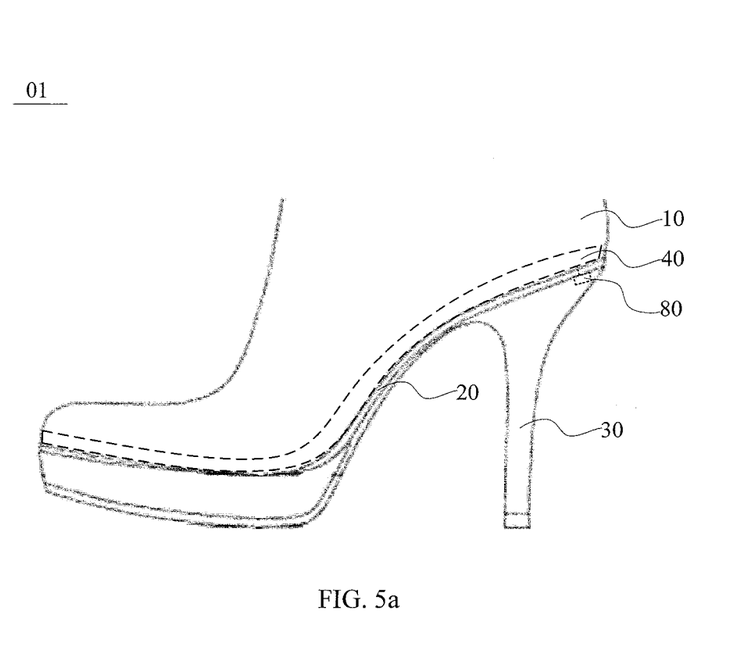
FIG. 5a is a schematic view of a fourth structure of a smart shoe according to an embodiment of the present disclosure.

Specifically, in a case that the smart shoe 01 does not comprise the processor 50, referring to FIG. 5a, the first communication module 80 is connected to the foot sole print recognition sensor 40 and is configured to transmit the foot sole print information acquired by the foot sole print recognition sensor 40 to an external terminal device, so that it is judged by the external terminal device whether or not the current user is the authenticated user, and it will alarm if the current user is a non-authenticated user.

Figure 5B:
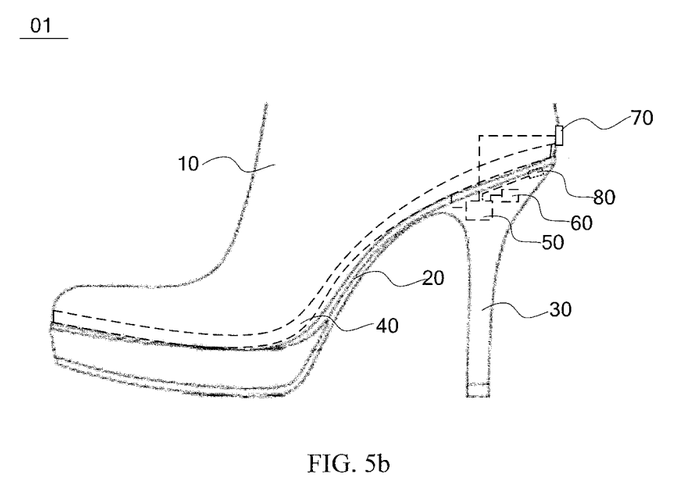
FIG. 5b is a schematic view of a fifth structure of a smart shoe according to an embodiment of the present disclosure.

In a case that the smart shoe 01 comprises the processor 50, referring to FIG. 5b, the first communication module 80 is connected to the processor 50 and is configured to transmit the alarm signal to the external terminal device, so as to facilitate the external terminal device to alarm.

The external terminal device, for example, includes a mobile phone, a tablet computer or the like.

It is considered that a shoe with a high heel will make a person taller and full of temperament, and accordingly is favored by most of the female. Accordingly, as shown in FIGS. 2, 4, 5a and 5b, the smart shoe according to these embodiments of the present disclosure preferably further comprises a heel 30.

Whatever, it is considered that, when walking, the center of gravity of body will naturally move upwards if a height of the heel is greater than 6 cm, and, a long time walking with a shoe having a heel of greater than 6 cm will have an impact on health, thus in these embodiments of the present disclosure, the heel 30 is manufactured to be retractable, so that a long time walking with the shoe having this heel will be avoided by adjusting a height of the heel 30.

Figure 6A:
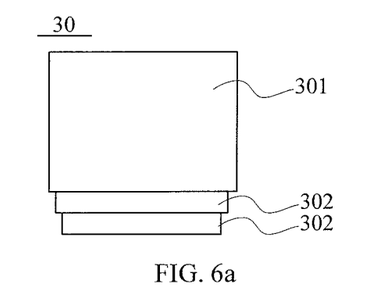
FIG. 6a is a structural schematic view showing a heel of a smart shoe according to an embodiment of the present disclosure when retracted completely.
Figure 6B:
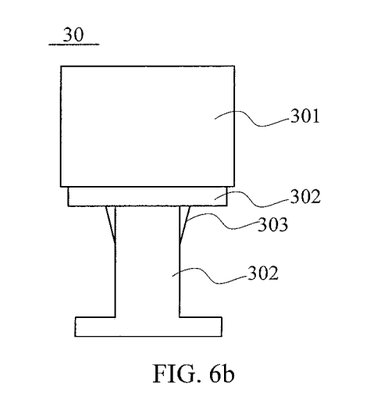
FIG. 6b is a structural schematic view showing the heel of the smart shoe according to the embodiment of the present disclosure when retracted partially.
Figure 6C:
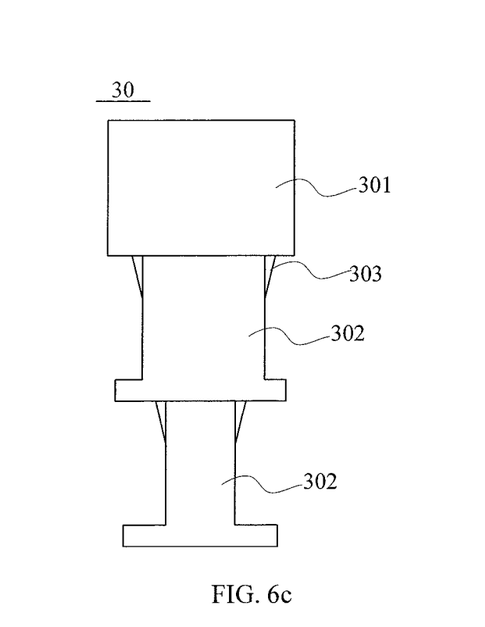
FIG. 6c is a structural schematic view showing the heel of the smart shoe according to the embodiment of the present disclosure when stretched completely.

Specifically, referring to FIGS. 6a, 6b, 6c, the heel 30 comprises a base part 301 of heel and at least one connecting part 302 of heel, and, the connecting parts 302 of heel and the base part 301 of heel are arranged to be nested into one another from top to bottom in sequence while the base part 301 of heel is fixedly connected to a rear end of the shoe sole 20.

In an example, the base part 301 of heel is hollow, and all the connecting parts 302 of heel, at most excepting the one which is farthest away from the base part 301 of heel, are hollow.

Herein, phrase "all the connecting parts 302 of heel, at most excepting the one which is farthest away from the base part 301 of heel, are hollow" means that, other connecting parts 302 of heel than the one which is farthest away from the base part 301 of heel are hollow; or, the base part 301 of heel and all the connecting parts 302 of heel are hollow. The reason why the base part 301 of heel and the connecting parts 302 of heel are manufactured to be hollow is in that, once the height of the heel 30 is reduced, a lower connecting part 302 of heel can be retracted into an upper connecting part 302 of heel or into the base part 301 of heel.

It should be mentioned that, FIGS. 6a, 6b, 6c illustrate an example in which two connecting parts 302 of heel are included, however, it is not limited to this in embodiments of the present disclosure. Heights of the connecting part 302 of heel and the base part 301 of heel and total height of the heel 30 may be chosen freely, and there is no limitation on this herein.

FIG. 6a shows a configuration in which all the connecting parts 302 of heel are retracted into the base part 301 of heel, FIG. 6b shows a configuration in which one connecting part 302 of heel, which is connected to the base part 301 of heel, is retracted into the base part 301 of heel, and, FIG. 6c shows a configuration in which all the connecting parts 302 of heel are stretched from the base part 301 of heel.

Moreover, referring to FIGS. 6b and 6c, the smart shoe 01 may further comprise elastic supports 303 disposed at side faces of the connecting part 302 of heel. The elastic supports 303 are capable of being retracted into the connecting part 302 of heel or being stretched from the connecting part 302 of heel, and are configured to secure the connecting part 302 of heel stretched from the base part 301 of heel or from another connecting part 302 of heel, being disposed above the stretched connecting part 301 of heel.

That is to say, for any one of the connecting parts 302 of heel, once it is needed to retract it into the base part 301 of heel or into another connecting part 302 of heel, being disposed above the any one of connecting part 301 of heel, the elastic supports 303 are pressed so that they are retracted into the corresponding connecting part 302 of heel, and then, the corresponding connecting part 302 of heel is pushed along a direction of height of the heel into the base part 301 of heel or into another connecting part 302 of heel, being disposed above the corresponding connecting part 301 of heel. Once it is needed to stretch a connecting part 302 of heel from the base part 301 of heel or from another connecting part 302 of heel, being disposed above the connecting part 302 of heel to be stretched, the connecting part 302 of heel to be stretched is pulled along the direction of height of the heel until a portion of the connecting part 302 of heel where the elastic supports 303 are provided is pulled out, and then the elastic supports 303 will unfold elastically without being pressed, to secure the stretched connecting part 302 of heel.

Moreover, referring to FIGS. 6b and 6c, the elastic support 303 is in a wedge shape, and a cross sectional area of the elastic support 303 is gradually decreased from top to bottom. As a result, it is convenient to be pressed.

Preferably, referring to FIGS. 6b and 6c, a cross sectional area in bottom of any one of the connecting parts 302 of heel is greater than a cross sectional area in top thereof. As a result, when a height of the heel 30 is too great, instable walking caused by the thin lowest connecting part 302 of heel can be avoided.

Figure 7:
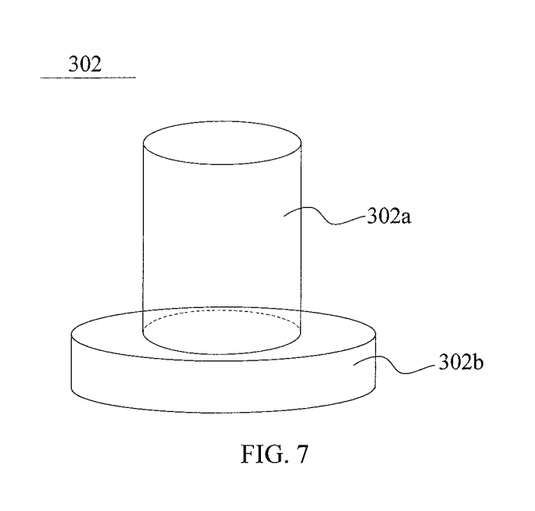
FIG. 7 is a structural schematic view showing a connecting part of heel in a heel of a smart shoe according to an embodiment of the present disclosure.

Moreover, preferably, referring to FIG. 7, the connecting part 302 of heel comprises a cylindrical main body 302a and a cylindrical base 302b, and a cross sectional area of the base 302b is greater than that of the main body 302a; and, central axes of the main body 302a and of the base 302b lie in one straight line.

It should be mentioned that, the base 302b is provided in embodiments of the present disclosure so that the smart shoe 01 will lead to a stable walking. Based on the above, it is understood by those skilled in the art that, the base 302b may never be retracted into the base part 301 of heel, once it is needed to retract it into the base part 301 of heel or into another connecting part 302 of heel, being disposed above the any one of connecting part 301 of heel.

Figure 8:
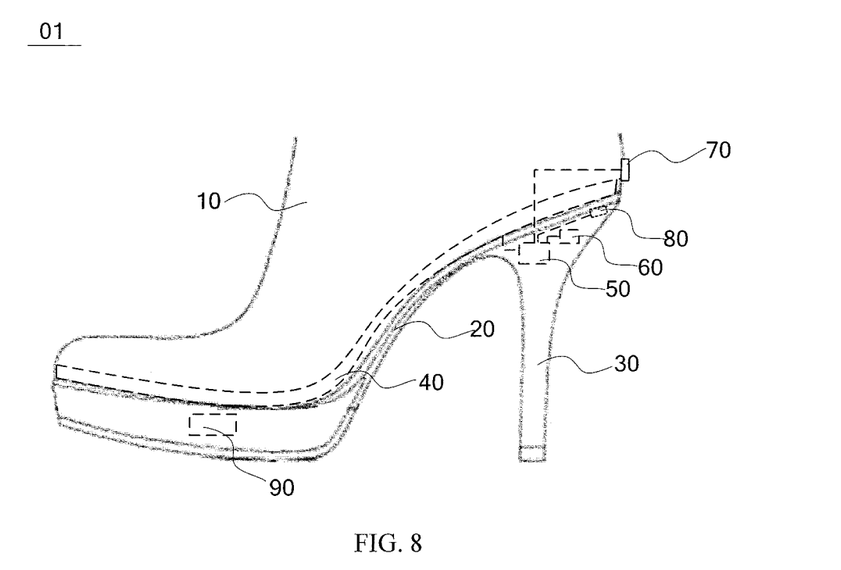
FIG. 8 is a schematic view of a sixth structure of a smart shoe according to an embodiment of the present disclosure.

Accordingly, referring to FIG. 8, the smart shoe 01 may further comprise a pedometer 90 configured to record walking data.

With provision of the pedometer 90 in embodiments of the present disclosure, the smart shoe 01 is provided with a walking data recording function, which may further enhance user's experience.

Based on the above, when the smart shoe 01 comprises the abovementioned heel 30, the height of the heel 30 can be adjusted according to the walking data, thereby eliminating some health problems caused by wearing a shoe having a heel of greater height.

Figure 9:
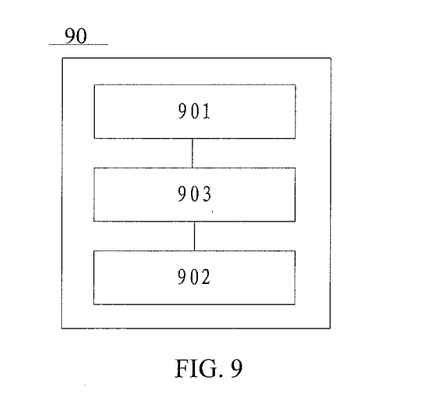
FIG. 9 is a functional schematic view of a pedometer in a smart shoe according to an embodiment of the present disclosure.

Moreover, preferably, referring to FIG. 9, the pedometer 90 comprises a step-counting sensing module 901 configured to acquire the walking data, a display module 902, and a control module 903 configured to display, through the display module 902 in real time, the walking data acquired by the step-counting sensing module 901.

As a result, with the display module 902 of the pedometer 90, the user of the shoe will achieve walking data in real time, so that, the user of the shoe may be remaindered to have a rest or may do some adjustments on height of the heel by himself/herself.

It should be mentioned that, locations of the step-counting sensing module 901, display module 902 and the control module 903 are not limited in these embodiments of the present disclosure, as long as the step-counting sensing module 901 is able to acquire walking data and the content displayed in the display module 902 can be seen.

Moreover, preferably, the walking data comprises number of steps and a travel time. The pedometer 90 comprises a switching button 904 connected to the control module 903 and configured to control, by the control module 903, the display module 902 to display the number of steps or the travel time.

Figure 10:
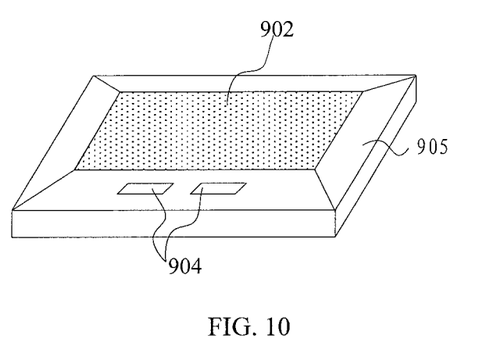
FIG. 10 is a schematic view showing location of a switching button in a smart shoe according to an embodiment of the present disclosure.

For example, as shown in FIG. 10, a housing 905 may be provided outside the display module 902, and the switching button 904 may be provided on the housing 905.

As a result, by operating the switching button 904, a user of the smart shoe 01 can easily view the number of steps or the travel time, upon which it is judged whether or not some adjustments on height of the heel should be done or to have a rest.

It should be mentioned that, location of the switching button is not limited in these embodiments of the present disclosure, as long as it can be operated conveniently.

Moreover, preferably, in a case that the smart shoe 01 comprises the heel 30, the control module 903 is further configured to send a reminder instruction to the display module 902 according to the height of the heel 30, when the number of steps or the travel time is greater than a present value. The display module 902 is also configured to display the reminder instruction sent by the control module 903.

As a result, through the reminder instruction displayed on the display module 902, the user may be remaindered by himself/herself to have a rest or to do some adjustments on height of the heel 30.

For example, provided that the heel 30 has a height of H and the travel time is T.

If H<4~6 cm, T can be set to be no more than 120 minutes, and a reminder for rest is given once it is greater than 120 minutes. If H<6~8 cm, T can be set to be no more than 60 minutes, and a reminder for health is given once it is greater than 60 minutes. If H>8 cm, T can be set to be no more than 45 minutes, and a reminder for health is given once it is greater than 45 minutes.

Figure 11:
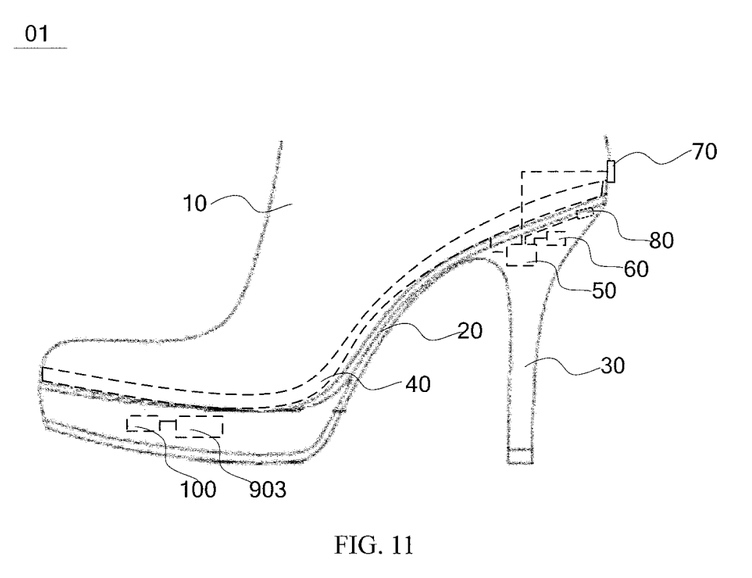
FIG. 11 is a schematic view of a seventh structure of a smart shoe according to an embodiment of the present disclosure.

Moreover, referring to FIG. 11, the smart shoe 01 may further comprise a second alarm 100 connected to the control module 903 and configured to alarm according to the reminder instruction sent by the control module 903. The second alarm 100 can be a buzzer.

In these embodiments of the present disclosure, the second alarm 100 can be disposed within the pedometer 90. Of course, the first alarm 70 and the second alarm 100 may be the same one. As a result, one alarm is omitted, and the cost is saved.

As a result, even the display module 902 display a corresponding reminder instruction but the corresponding reminder instruction is not seen by the user of the smart shoe 01, the second alarm 100 still alarms so that a sound reminder is given to the user.

Figure 12:
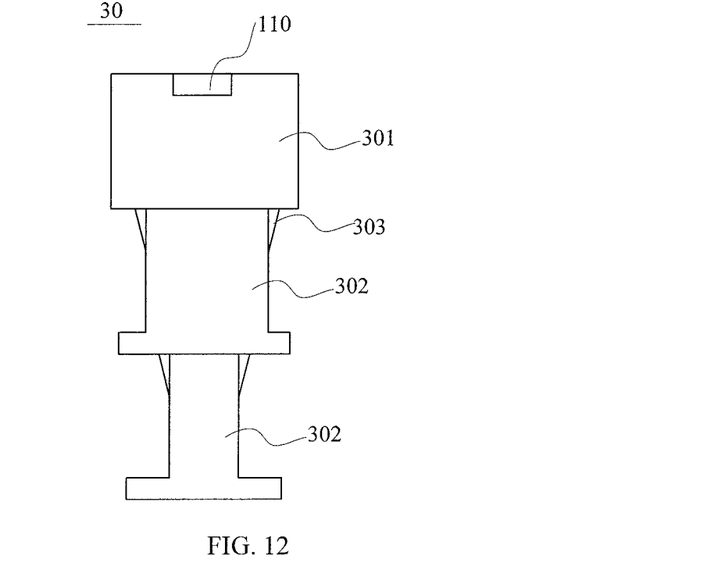
FIG. 12 is a structural schematic view showing another heel of a smart shoe according to an embodiment of the present disclosure.

The abovementioned acquisition of a height of the heel 30 can be implemented by measuring the height of the heel 30 by means of a position sensor 110, referring to FIG. 12. The position sensor 110 is connected to the control module 903, and is disposed at a location where the base part 301 of heel contacts the shoe sole 20 and outside of the base part 301 of heel.

Figure 13:
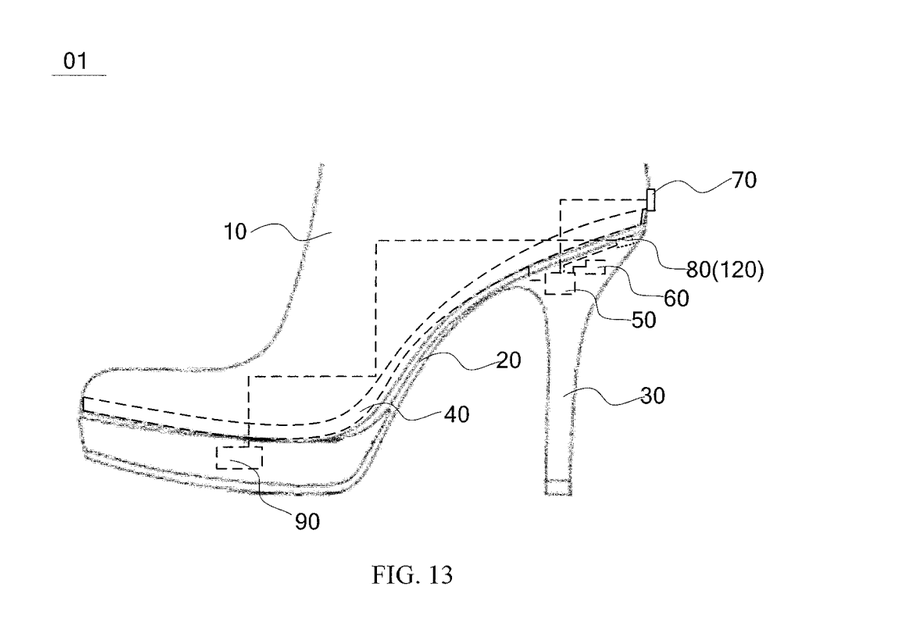
FIG. 13 is a schematic view of an eighth structure of a smart shoe according to an embodiment of the present disclosure.

Preferably, referring to FIG. 13, the smart shoe 01 further comprises a second communication module 120 connected to the pedometer 90 and configured to transmit the walking data to an external terminal device.

As a result, the external terminal device such as a mobile phone can obtain walking data in real time or can obtain walking data within certain time, so that, the user of the shoe may learn his/her walking conditions and thus user's experience is enhanced.

Moreover, preferably, in a case that the smart shoe 01 comprises the first communication module 80, the first communication module 80 and the second communication module 120 are the same one.

As a result, one communication module is saved and the cost is reduced.

Figure 14:
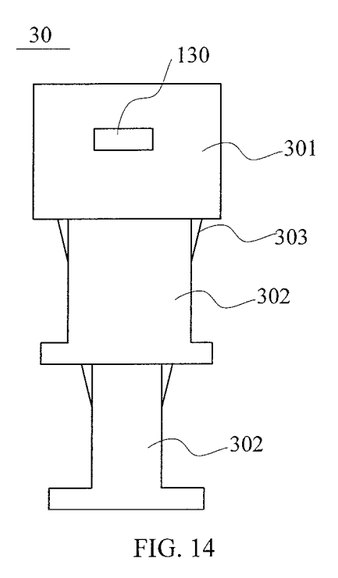
FIG. 14 is a structural schematic view showing still another heel of a smart shoe according to an embodiment of the present disclosure.

Accordingly, preferably, the smart shoe 01 further comprises a power supply module configured to provide electric power and a charging interface 130 configured for charging of the power supply module. Referring to FIG. 14, the charging interface 130 is disposed on the base part 301 of heel. As a result, it is convenient to implement an electrical charging.

The above description is merely used to illustrate particular embodiments of the present disclosure, but not to limit the present disclosure. It should be understood by those skilled in the art that, all of changes and replacements made easily within principles and spirit of the present disclosure should be included within the scope of the present disclosure. Therefore, the scope of the present disclosure is defined in the claims of the present disclosure.

What is claimed is:

1. A smart shoe, comprising an upper, a shoe sole and a foot sole print recognition sensor disposed in the shoe sole;
    wherein, the foot sole print recognition sensor is configured to acquire foot sole print information of a user who wears the smart shoe;
    the smart shoe further comprises a processor, a storage and a first alarm;
    the processor is connected respectively to the foot sole print recognition sensor, the storage and the first alarm;
    the storage is configured to store foot sole print information;
    the processor is configured to receive the foot sole print information acquired by the foot sole print recognition sensor, to match the received foot sole print information with the stored foot sole print information in the storage, and, to send an alarm signal if they do not match with each other; and
    the first alarm is configured to receive the alarm signal sent by the processor and to alarm.

2. The smart shoe of claim 1, wherein the foot sole print recognition sensor comprises any one of a radio frequency type foot sole print recognition sensor, an optical-type foot sole print recognition sensor, a capacitive-type foot sole print recognition sensor and an ultrasonic-type foot sole print recognition sensor.

3. The smart shoe of claim 1, wherein the smart shoe further comprises a first communication module;
    the first communication module is configured to transmit the foot sole print information acquired by the foot sole print recognition sensor to an external terminal device.

4. The smart shoe of claim 3, wherein, the first communication module is also configured to transmit the alarm signal sent by the processor to the external terminal device.

5. The smart shoe of claim 1, wherein the smart shoe further comprises a heel comprising a base part of heel and at least one connecting parts of heel, and, the connecting parts of heel and the base part of heel are arranged to be nested into one another from top to bottom in sequence while the base part of heel is fixedly connected to a rear end of the shoe sole;
    wherein, the base part of heel is hollow, and all the connecting parts of heel, at most excepting the one which is farthest away from the base part of heel, are hollow.

6. The smart shoe of claim 5, wherein the smart shoe further comprises an elastic support disposed at a side face of the connecting part of heel, being retractable into the connecting part of heel or being stretchable from the connecting part of heel, and being configured to secure the connecting part of heel stretched from the base part of heel or from another connecting part of heel, being disposed above the stretched connecting part of heel.

7. The smart shoe of claim 6, wherein the elastic support is in a wedge shape, and a cross sectional area of the elastic support is gradually decreased from top to bottom.

8. The smart shoe of claim 5, wherein a cross sectional area of a bottom of any one of the connecting parts of heel is greater than a cross sectional area of a top thereof.

9. The smart shoe of claim 8, wherein the connecting part of heel comprises a cylindrical main body and a cylindrical base, and a cross sectional area of the base is greater than that of the main body; and
    central axes of the main body and of the base lie in one straight line.

10. The smart shoe of claim 1, wherein the smart shoe further comprises a pedometer configured to record walking data.

11. The smart shoe of claim 10, wherein the pedometer comprises a step-counting sensing module configured to acquire the walking data, a display module, and a control module configured to display, through the display module in real time, the walking data acquired by the step-counting sensing module.

12. The smart shoe of claim 11, wherein the walking data comprises number of steps and a travel time;
the pedometer further comprises a switching button connected to the control module and configured to control, by the control module, the display module to display the number of steps or the travel time.

13. The smart shoe of claim 12, wherein in a case that the smart shoe comprises a heel, the control module is further configured to send a reminder instruction to the display module according to a height of the heel when the number of steps or the travel time is greater than a present value; and
the display module is also configured to display the reminder instruction sent by the control module.

14. The smart shoe of claim 13, wherein the smart shoe further comprises a second alarm connected to the control module and configured to alarm according to the reminder instruction sent by the control module.

15. The smart shoe of claim 13, wherein the smart shoe further comprises a position sensor connected to the control module, being disposed at a location where the base part of heel contacts the shoe sole and outside of the base part of heel, and being configured to measure the height of the heel.

16. The smart shoe of claim 10, wherein the smart shoe comprises a second communication module connected to the pedometer and configured to transmit the walking data to an external terminal device.

17. The smart shoe of claim 16, wherein in a case that the smart shoe comprises a first communication module, the first communication module and the second communication module are the same one.

18. The smart shoe of claim 1, wherein the smart shoe further comprises a power supply module configured to provide an electric power, and a charging interface disposed on the base part of heel and configured for charging of the power supply module.

* * * * *